United States Patent
Prywes

(10) Patent No.: US 7,655,831 B2
(45) Date of Patent: Feb. 2, 2010

(54) METHOD FOR FLUID CONTROL IN MEDICAL APPLICATIONS

(76) Inventor: Arnold S. Prywes, 12 Jason Ct., Dix Hills, NY (US) 11746

(*) Notice: Subject to any disclaimer, the term of this patent is extended or adjusted under 35 U.S.C. 154(b) by 266 days.

(21) Appl. No.: 11/582,855

(22) Filed: Oct. 18, 2006

(65) Prior Publication Data

US 2007/0185468 A1   Aug. 9, 2007

Related U.S. Application Data

(60) Provisional application No. 60/728,218, filed on Oct. 19, 2005.

(51) Int. Cl.
*A61F 13/53* (2006.01)

(52) U.S. Cl. .............. 604/369; 604/286; 604/517; 604/262

(58) Field of Classification Search .............. 600/30; 604/369, 286, 517, 544; 401/262
See application file for complete search history.

(56) References Cited

U.S. PATENT DOCUMENTS

| | | | | |
|---|---|---|---|---|
| 211,104 A * | 1/1879 | Mulford | ............ | 401/183 |
| 977,825 A * | 12/1910 | Murphy | ............ | 604/1 |
| 1,897,423 A * | 2/1933 | Ferri | ............ | 604/286 |
| 2,763,266 A * | 9/1956 | Evans | ............ | 604/540 |
| 2,898,913 A * | 8/1959 | Ritter et al. | ............ | 604/368 |
| 3,084,689 A * | 4/1963 | Dankwardt et al. | ............ | 604/286 |
| 3,095,877 A * | 7/1963 | Rowan | ............ | 604/93.01 |
| 3,362,400 A * | 1/1968 | De Bella | ............ | 600/575 |
| 3,373,746 A * | 3/1968 | White et al. | ............ | 604/328 |
| 3,386,927 A * | 6/1968 | Rosecrans et al. | ............ | 521/112 |
| 3,789,828 A * | 2/1974 | Schulte | ............ | 600/30 |
| 4,133,303 A * | 1/1979 | Patel | ............ | 600/587 |
| 4,248,214 A * | 2/1981 | Hannah et al. | ............ | 604/523 |
| 5,071,429 A * | 12/1991 | Pinchuk et al. | ............ | 606/192 |
| 5,433,782 A * | 7/1995 | Filbert et al. | ............ | 118/266 |
| 5,513,660 A * | 5/1996 | Simon et al. | ............ | 128/885 |
| 5,671,755 A * | 9/1997 | Simon et al. | ............ | 128/885 |
| 5,843,060 A * | 12/1998 | Cercone | ............ | 604/369 |
| 5,867,929 A * | 2/1999 | Jung et al. | ............ | 47/40.5 |
| 6,007,511 A * | 12/1999 | Prywes | ............ | 604/9 |
| 6,569,081 B1 * | 5/2003 | Nielsen et al. | ............ | 600/32 |
| 6,700,511 B1 | 3/2004 | Chang et al. | | |
| 6,740,333 B2 * | 5/2004 | Beckett et al. | ............ | 424/436 |
| 7,267,670 B2 * | 9/2007 | Mulholland et al. | ............ | 604/517 |

(Continued)

*Primary Examiner*—Tatyana Zalukaeva
*Assistant Examiner*—Paula L Craig
(74) *Attorney, Agent, or Firm*—Ladas and Parry LLP

(57) ABSTRACT

A method and device for shunting fluid from high pressure volumes to low pressure volumes to treat various medical problems caused by an imbalance or malfunction of the regulation of flow between these volumes. Typical problems where the method and device are employed include the treatment of incontinence, treatment of hydrocephalus, treatment of elevated intra-cranial pressure, treatment of elevated intra-ocular pressure and the like. The controlled release of fluid from the high pressure volume is accomplished by inserting a sponge using an insertion device such as an endoscope. The sponge retains and releases fluid in response to a pressure differential between the high and lower pressure volumes. The sponge material may be natural or synthetic and sponges with different porosity and fluid retention are provided to achieve desired flow characteristics. The sponges can be provided with different shapes to allow it to conform to the anatomy and may have additional or integral modules that attach it to the anatomical structures.

8 Claims, 4 Drawing Sheets

U.S. PATENT DOCUMENTS

| | | | |
|---|---|---|---|
| 2001/0016716 A1* | 8/2001 | Mulholland | 604/288 |
| 2002/0151923 A1* | 10/2002 | Holzer | 606/193 |
| 2002/0176893 A1* | 11/2002 | Wironen et al. | 424/489 |
| 2003/0208137 A1* | 11/2003 | Schmidt et al. | 600/573 |
| 2005/0171563 A1* | 8/2005 | Heinrich et al. | 606/153 |
| 2006/0135921 A1* | 6/2006 | Wiercinski et al. | 604/368 |

* cited by examiner

METHOD FOR FLUID CONTROL IN MEDICAL APPLICATIONS

CROSS-REFERENCE TO RELATED APPLICATIONS

The present invention claims the benefit of U.S. Provisional Patent Application No. 60/728,218 filed Oct. 19, 2005, which is hereby incorporated by reference in its entirety.

FIELD OF THE INVENTION

The present invention relates to the use of a sponge apparatus and its methods of insertion. The invention seeks to maintain control of fluid flow between two volumes and is suitable for surgical implantation.

BACKGROUND OF THE INVENTION

In the field of medicine, the requirement for the control of flow of fluids from high to low pressure volumes is required in many organs. Disorders of control of flow produce medical conditions for which medical or surgical treatment is required. Heretofore medical and surgical interventions have associated side effects and complications that prevent the conditions from being adequately treated.

A specific example is urinary incontinence which is a common condition whereby the orderly outflow of urine from the bladder into the urethra is disordered by anatomical and neural disorders. The American Urological Association states as follows:

"urinary incontinence is the involuntary loss of urine. It is not a disease but rather a symptom that can be caused by a wide range of conditions. Diabetes, stroke, multiple sclerosis, Parkinson's disease, some surgeries or even childbirth can cause incontinence. More than 15 million Americans, mostly women, suffer from incontinence. Although it is more common in women over 60, it can occur at any age. Most health-care professionals classify incontinence by its symptoms or circumstances in which it occurs. In the normal population, the incidence of incontinence in females over 65 is more than 25 percent and in males it is about 15 percent"

This dysfunction produces a requirement for the use of diapers, pessaries, medications and surgical procedures that are not successful in controlling the condition in a large number of patients. One such procedure involves implantation of an artificial sphincter, in the form of a patient-controlled device made of silicone rubber with an inflatable cuff that fits around the urethra, (the tube through which urine leaves the bladder). A balloon regulates the pressure of the cuff, and a bulb controls inflation and deflation of the cuff. The balloon is placed within the pelvic space, and the control bulb is placed in the scrotum of a male or the external vaginal lips of a female. The cuff is inflated to keep urine from leaking. When urination is desired, the cuff is deflated, allowing urine to drain out.

Numerous other medical conditions exist in which fluid control is required such as hydrocephalus glaucoma and the like which will be described more fully later.

SUMMARY OF THE INVENTION

An object of the invention is to provide a sponge device and associated method for controlling fluid flow from a chamber, wherein the sponge device is inserted in proximity to an outlet of the chamber to serve as a flow control means to regulate and control outflow of fluid from the chamber.

According to the invention the sponge device can be utilized to control urine flow from the bladder in order to treat incontinence.

In further accordance with the invention, the sponge device can be used to control fluid outflow from the anterior chamber of the eye for treatment of glaucoma.

According to the invention, the sponge device can be used to control outflow of fluid from the brain to control hydrocephalus.

According to the invention, the flow control device and its associated methods of insertion serve in general for placement of the sponge device for use in a multiplicity of surgical procedures.

The sponge device comprises a multiplicity of sponges having different permeabilities to provide different fluid retentive flow rates and pressure sensitive characteristics that control pressure within organs and anatomical structures.

In further accordance with the invention, the sponges can be provided with a multiplicity of shapes, each conforming to the anatomic structure in which it is to be inserted and attached.

The sponges can be made of non-absorbable or absorbable material which maintains its anatomical position when made of non-absorbable material and allows unimpeded flow when made of absorbable material.

The sponge device may be simple or compound and the sponge can be attached to a tube, within a tube, and shaped as a tube, or the like, with or without modifications of the sponge or tube to allow insertion and maintenance of the location of the device in its desired anatomic location The sponge device may be attached by a plurality of means including mechanical (hooks, barbs, flanges and the like), physical (shape, contour, surface modifications and the like), chemical (adhesives, tissue glues, coatings and the like). The sponge device may be inserted using devices unique to the anatomic area in which the device is to be inserted.

The sponge device may have radio-opaque, sonographic, fluorescent, magnetic indicia which allow identification of the device in the proper position and it may have attached means for flow measurement using modular or integral means to transmit data to external monitors. The measurement means may be temporary or permanent.

The sponge device may have appended flow and pressure transducers/controllers to modify the characteristics of the sponge architecture using a chemical, electrical, mechanical, optical, thermal, biochemical or biological means or the like thereby allowing greater or lesser flow as required to attain optimal flow characteristics. Signals to the pressure transducer/controllers can be transmitted wirelessly by RF, IR or the like.

The sponge device may be manufactured using nanotechnology to produce the devices and modules for measurement and modification and control of sponge architecture and thereby allowing greater or lesser flow as required to attain optimal flow characteristics.

The sponge device can provide extremely low resistance or restriction thereby allowing normal flow characteristics or it may produce complete flow restriction to occlude flow, temporarily, or permanently.

The sponge device may act as a filter to bacteria and other microorganisms temporarily or permanently which may be employed in maintaining fistulas for repeat use as in venous or arterial dialysis sites, chemotherapy infusion. It can also be used in an ostomy site for maintenance thereof.

The sponge device may be used as a drainage device substituting for drainage tubes after gastrointestinal, urological, cardiothoracic, neurosurgical, head and neck surgery, and the like where serous, sero-sanguinous, mucoid, pyogenic, and other discharge of fluids is required.

The sponge device may have attached pharmaceutical modules or have inherent pharmaceutical activity which may increase or decrease flow, resistance, pressure and or modify immune response, inflammation, antibiotic or chemotherapeutic response.

The sponge device may be modified to filter out undesired cells and aid their destruction by their configuration or by the combination of chemotherapeutic, immunologic, electrostatic, configurational, pharmaceutical, or physical properties thereby reducing hematologic and/or other cancer cells and the like.

The sponge device may have appended tube attachments for the permanent implantation into vessels, abdominal organs, intestines, and the like whereby fistulas remain patent with replaceable or absorbable sponge implants modified to act as a stopper or occluder which could be replaced and provided with means for maintaining patency by chemical, pharmaceutical, physical, biological, antiviral, antibacterial and filtration means and the like which are appended to or integral to the sponge implant.

The present invention is also applicable to control of urinary outflow by occluding the bladder at its outflow point at the junction to the urethra. Insertion of the device is accomplished by the use of a cystoscope with placement of the device at this junction. Internally the device controls outflow by releasing fluid only when sudden marked increase in intraluminal (bladder) pressure results in release of urine into the urethra. The fluid retentive property of the sponge implant prevents outflow of urine until a sudden increase in pressure on the bladder transmits pressure to the sponge resulting in outflow through the urethra.

The invention is also applicable for flow control in the treatment of hydrocephalus. Hydrocephalus occurs when the flow of fluid (cerebrospinal fluid or CSF) around the brain and spinal cord is impaired. CSF is produced in ventricles, which are cavities within the brain. The CSF surrounds the brain and spinal cord, providing nutrients, removing metabolic waste and cushioning the neural elements.

Increased pressure within the cavities produces secondary damage to the brain and neural elements of the spinal cord. In infants and children increased head circumference, altered brain contours with enlargement of the ventricles and resulting dysfunction occur. In older individuals the head circumference remains the same but pressure on the brain produces symptoms of dementia and other neurological dysfunction.

According to one treatment method the floor of the third ventricle in the brain is opened with a cutting means, to form an ostium allowing flow from the third ventricle into the basal cistern for absorption into the body.

According to the invention the sponge device is installed into the ostium formed in the floor of the third ventricle to provide flow control of the fluid from the third ventricle to the basal cisterns.

According to another method for relieving fluid pressure in the brain of a patient suffering from hydrocephalus a shunt system of tubes (catheters) connect the third ventricle into the abdominal (peritoneal) cavity. This method involved the disadvantage of possible infection or occlusion the shunt tubes.

By controlling the flow from the third ventricle to the basal cistern with the sponge device of the invention, the need for a placement of shunt tubes can be obviated. Nevertheless, in order to control the fluid flow the shunt tubes system itself can be fitted with sponge devices according to the invention.

An additional area of medical concern with regard to flow occurs within the eye. Increased pressure within the eye (IOP) is present in the conditions of ocular hypertension and glaucoma and may lead to visual loss and blindness. According to the Johns Hopkins University Dana Center for Preventive Ophthalmology, open-angle glaucoma affects more than 2 million individuals in the United States. Owing to the rapid aging of the US population, this number will increase to more than 3 million by 2020. Medical and surgical treatment of glaucoma is expensive and associated with side affects and complications. The significant cost of medications (eye drops) for glaucoma treatment may be as high as $3000 per patient per year. The need for constant use of medications, difficulty with non-compliance with medical treatment and the failure rate of glaucoma surgery is significant. The side effects and complications of surgical drainage procedures (trabeculectomy and glaucoma drainage device implants) are significant with failure occurring early and late in some individuals. The rapid and simple drainage procedure performed using the sponge device implant maintains constant controlled flow while keeping the fistula open.

An additional concern in diseases of organs where fluid flows from one area to another, the sponge device can act to restrict spread of toxins, cancer cells or the like from one area to another by filtering and concomitantly treating the disease. One such area is in the biliary tree or gall bladder where the device can be inserted using an endoscopic device or laparoscopically.

DETAILED DESCRIPTION

Figure 1:
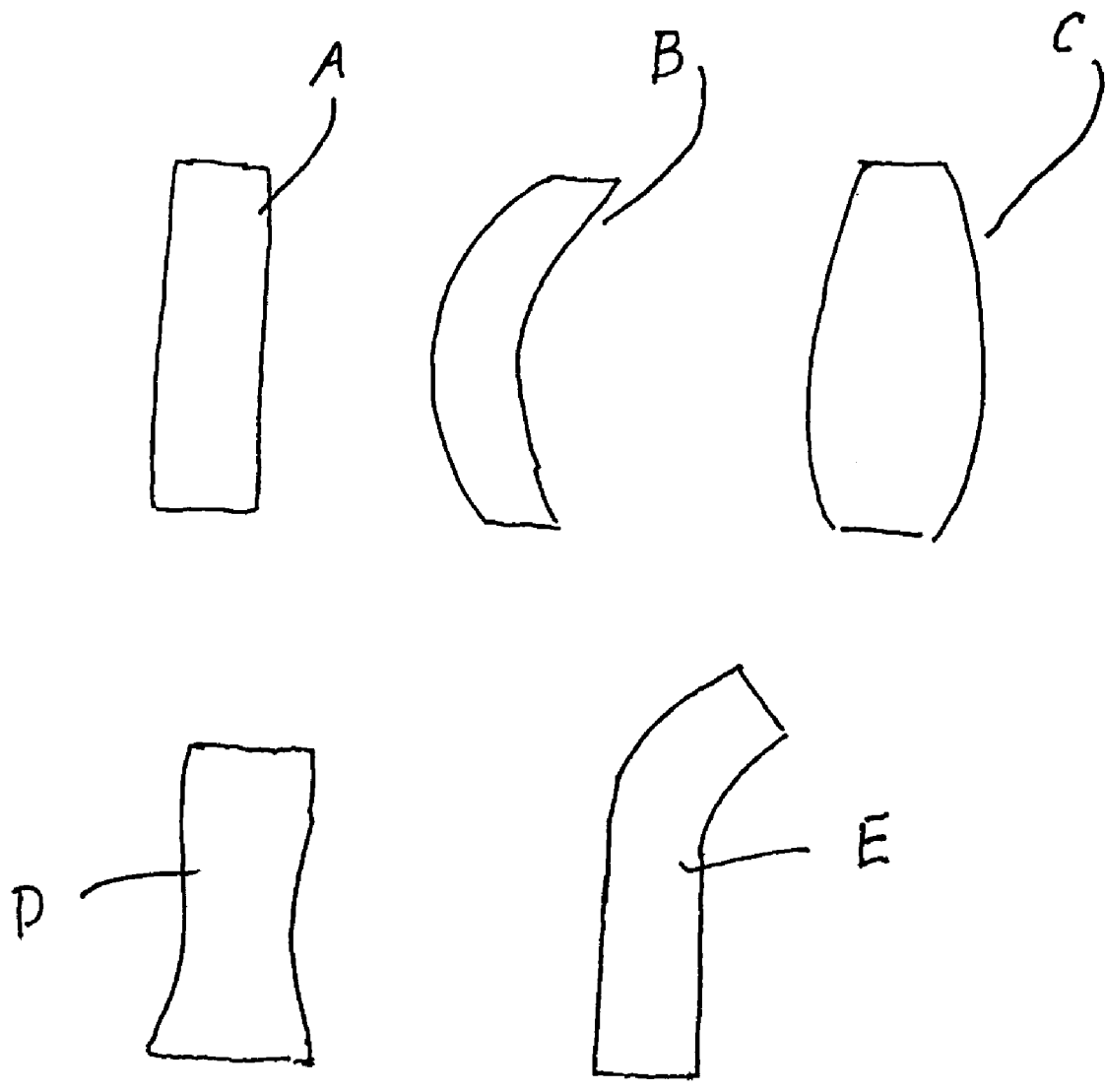
FIG. 1 is a diagrammatic illustration showing a number of sponges of different shape and size according to the present invention.

FIG. 1 shows a plurality of sponges A-E according to the invention. The sponges A-E have shapes adapted for the particular anatomical structure in which they are to be inserted. The shapes of the sponges which have been illustrated are merely exemplary. A greater number of shapes of the sponges can be adapted to the particular anatomical structure.

As particularly illustrated, sponge A is essentially cylindrical; sponge B is of curved cylindrical shape; sponge C has a wider aspect in its central region; sponge D narrows in its central region; sponge E is a composite of a straight cylindrical portion and a curved cylindrical portion.

Each of the sponges of different shape has a range of porosity varying from one extreme to provide occlusion to another extreme to provide free flow. The mode of varying the porosity of the sponges is well known to those skilled in the art and is not discussed in detail herein.

The sponges are made of a material inert to humans. The sponge can be made of natural or artificial material, preferably of plastic material including polypropylene, silicone, polymethylmethacrylate, polyglactin, polyamides, polyglycolic acid and the like. The sponges can be absorbent or non-absorbent depending on its use. The sponge can also be provided with a range of flexibilities depending on the anatomic structure into which it is to be inserted and its functions.

Several embodiments of the use of the sponge will be illustrated hereafter in various anatomic structures in order to control fluid flow to aid in treatment of a patient.

Figure 2:
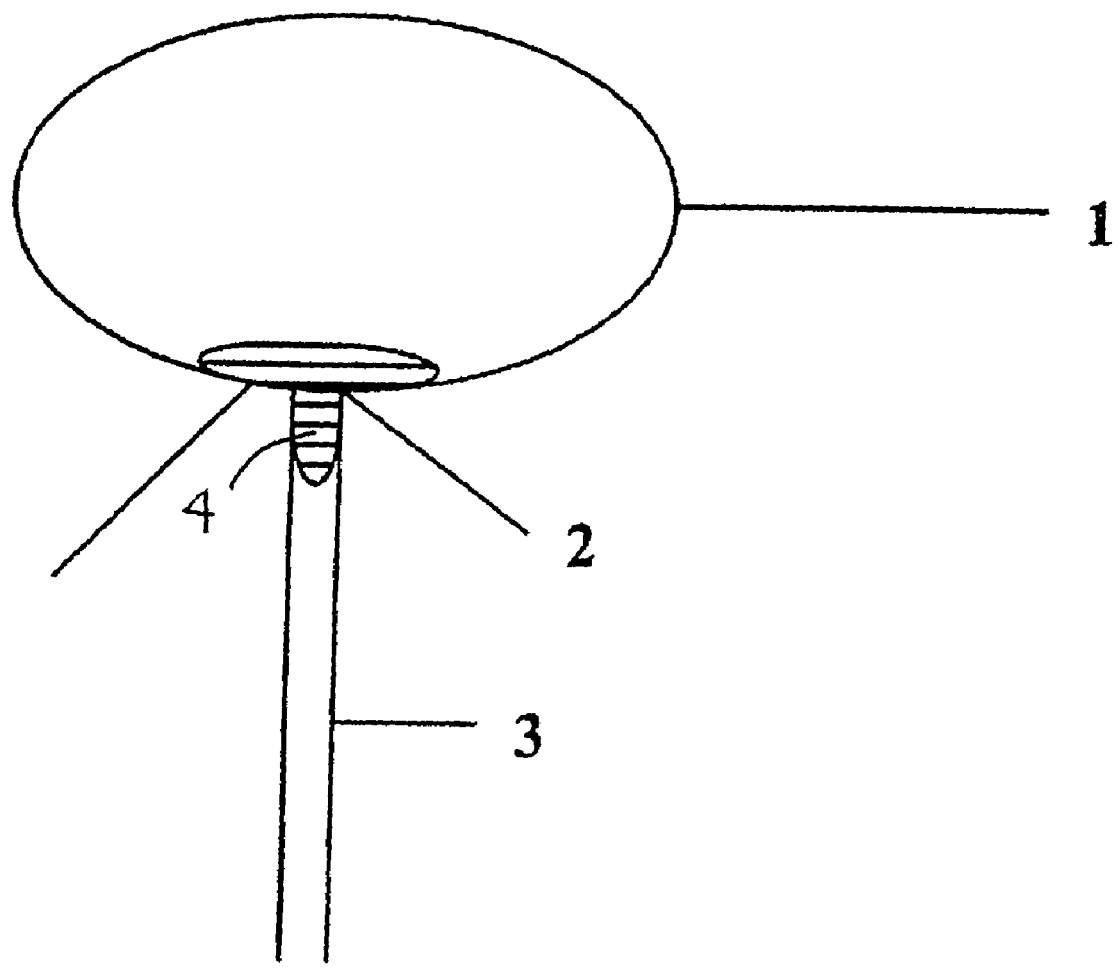
FIG. 2 diagrammatically illustrates the bladder and urethra in which the sponge is used for urinary control.
Figure 3:
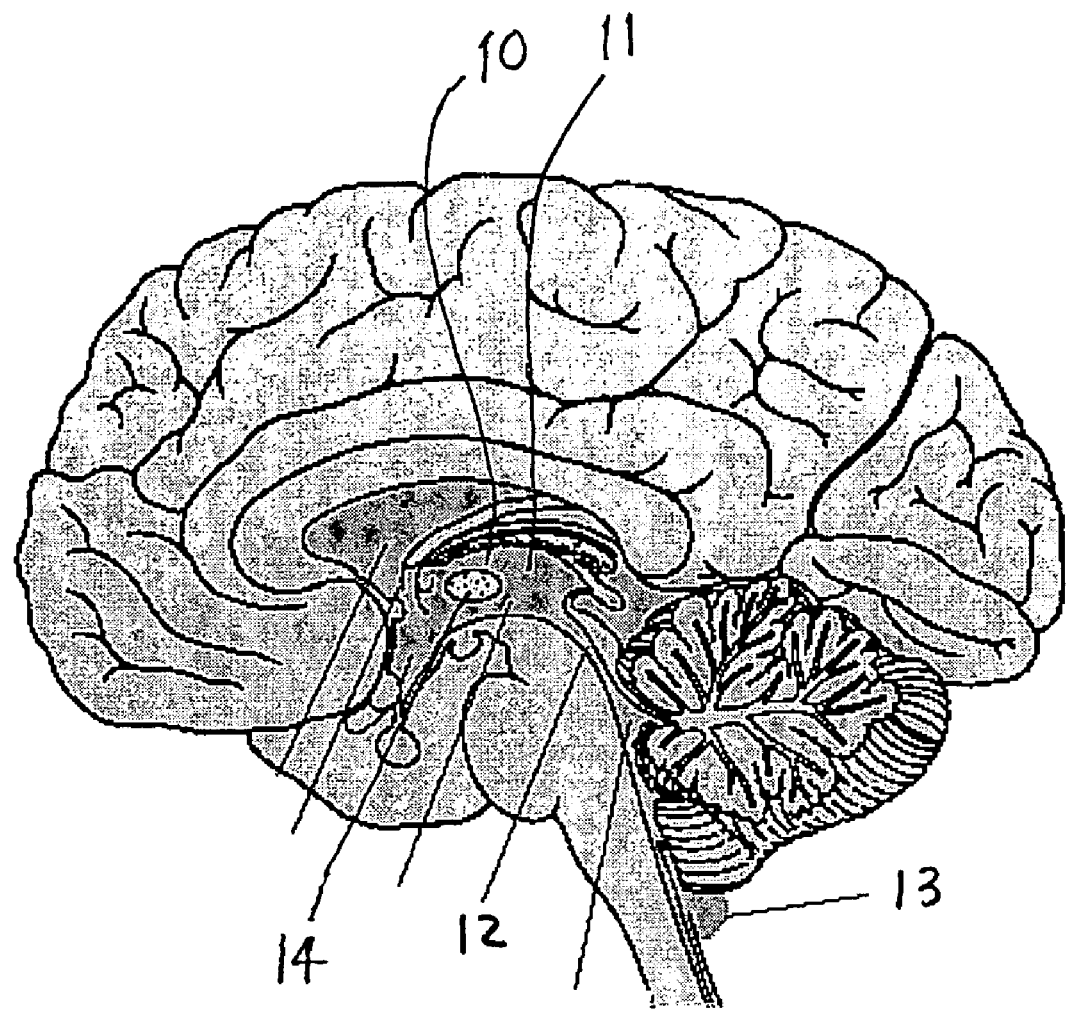
FIG. 3 is a diagrammatic illustration of the brain in which the sponge is used for controlling drainage.

FIG. 2 shows a system for control of urinary outflow for treatment of incontinence. In particular, the control of urinary outflow is achieved by temporary occluding the bladder (1) and its point of outflow at the junction (2) with the urethra (3). Control of the outflow from the bladder is achieved by insertion of a sponge (4) of the invention at the junction (2). The insertion of the sponge and placement at junction (2) is accomplished by the use of a cystoscope (not shown). Internally the sponge controls outflow by releasing fluid only when sudden marked increase in intra luminal (bladder) pressure results in release of urine into the urethra. The fluid retentive properties of the implanted sponge prevents outflow of urine until a sudden increase of pressure on the bladder transmits pressure to the sponge resulting in outflow through the urethra. In this treatment method, the sponge occludes outflow into the urethra thus preventing leakage therein and consequent incontinence. The sponge acts as a flow control valve which prevents such leakage and permits outflow only when the bladder generates a spontaneous increase in pressure. As was previously explained, the sponge that is selected for placement at the junction (2) will be anatomically adapted to the structure and will have a selected porosity to occlude outflow under normal pressure but to allow outflow when the bladder stimulates sudden increase in pressure.

Another condition adapted for use with the sponge of the invention is in the condition of hydrocephalus. Hydrocephalus occurs when the flow of fluid (cerebral spinal fluid or CSF) around the brain and spinal cord is impaired. CSF is produced in ventricles which are cavities within the brain. The CSF surrounds the brain and spinal cord providing nutrients, removing metabolic waste and cushioning the neural elements.

Increased pressure within the cavities produces secondary damage to the brain and neural elements of the spinal cord. In infants and children, increased head circumference, altered brain contours with enlargement of the ventricles and resulting dysfunction occur.

In order to treat this condition, it is known to produce an ostium 10 (hole) in the floor 11 of the third ventricle 12 allowing flow from the third ventricle into the basal cisterns 13.

In accordance with the present invention, a sponge 14 of suitable size, shape and porosity is inserted into the ostium and secured therein. The sponge provides two functions. The first is to maintain a controlled pressure of discharge fluid from the third ventricle to the basal cistern, and the second function is to prevent occlusion of the ostium in the third ventricle. In the latter respect, the sponge prevents scarring of the ostium. The insertion of the implant within the ostium 10 in the floor of the third ventricle also serves to prevent tissue growth over the ostium. If, after a significant period of time, the sponge is absorbed, the result will be a permanent ostium thus eliminating or reducing the requirement for subsequent surgeries. Alternatively, a second sponge can be placed in the ostium.

Figure 4:
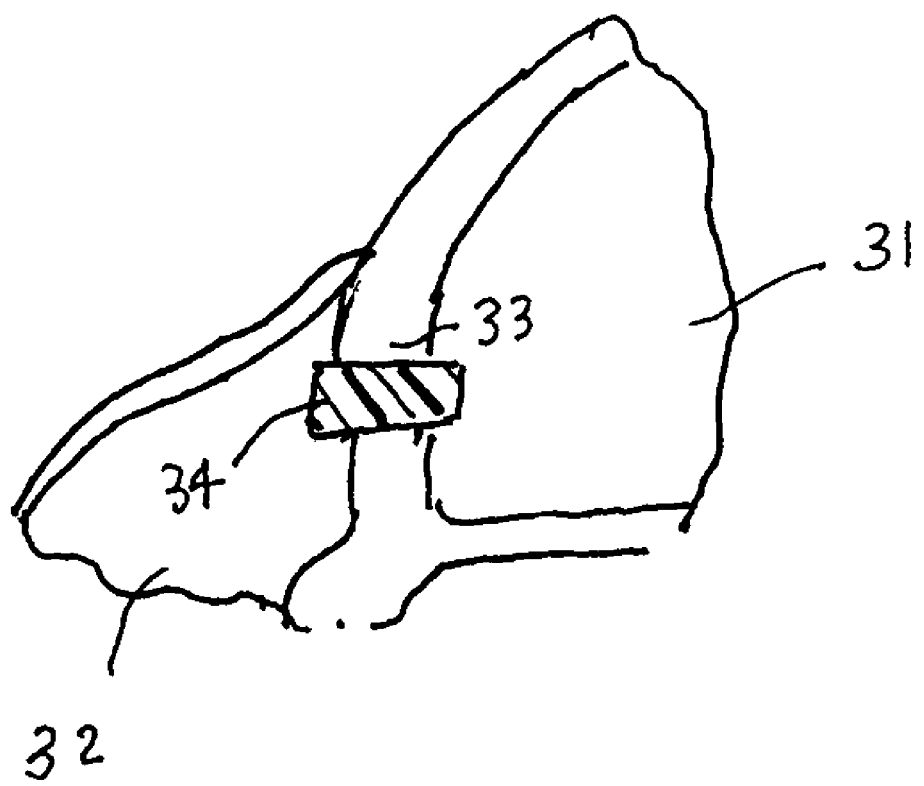
FIG. 4 diagrammatically illustrates the sponge for controlling intra-ocular pressure in the eye.

FIG. 4 shows the use of the sponge according to the invention in another area of medicine, namely in controlling intra-ocular pressure within the eye. In FIG. 4 numeral 31 designates the anterior chamber of the eye and numeral 32 designates the sub-conjunctival space. Under normal conditions, the intra-ocular pressure of the fluid in the anterior chamber drains into the sub-conjunctival space and normal pressures prevail. However, in conditions of glaucoma the intra-ocular pressure increases and unless the pressure is relieved, either by medication or by surgery, damage to the optic nerve can develop. In one form of surgery a fistula 33 (hole) is formed in the sclera (34) which separates the anterior chamber and the sub-conjunctival space in order to provide an outflow path for drainage of the fluid in the anterior chamber and release of pressure. I have previously disclosed in U.S. Pat. No. 6,007,511 control means to regulate the pressure flow. The sponge of the invention as shown at (35) serves as a flow control means to regulate the outflow of fluid from the anterior chamber to the sub-conjunctival space. By selecting the porosity of the sponge, flow control can be closely regulated and controlled intra-ocular pressure can be maintained in the eye.

The sponge of the invention has been described above in relation to several methods of medical treatment and it will be apparent to those skilled in the art that many other treatments in which flow control between one volume and another can be achieved.

The composition and nature of the porosity and absorptive-retentive characteristics of the sponge device in differential use allow for differences in flow characteristics. The acute changes in pressure required for sudden release of bladder contents into the urethra for the treatment of incontinence mandates higher pressure resistance of the device, as in contrast to the treatment of high intracranial or intra-ocular pressure where constant flow and lower flow rates and volumes are required. Thus the sponge implant's fluid permeability characteristics allow constant flow while maintaining intracranial and intra-ocular pressure thereby maintaining the appropriate volumes of cerebrospinal fluid and aqueous fluid respectively.

Although, I do not wish to be bound by any theory as to how the sponge device of the invention is particularly effective for the purposes indicated, it is believed that because of the great multitude of open cells or pores providing multiple pathways for absorption and flow, there is little opportunity for permanent clogging or occlusion whereby the sponge device can function reliably, particularly over long periods of time.

While the invention has been described with reference to several embodiments, it will become apparent to those skilled in the art that numerous modifications and variations can be made without departing from the scope and spirit of the invention as defined in the attached claims.

What is claimed is:

1. A method of controlling flow of a fluid from a first volume to a second volume, the first volume being at a higher increasable pressure than the second volume, the method comprising inserting a sponge in a flow path between the first and second volumes, said sponge being constructed and arranged to occlude flow of the fluid from said first volume to said second volume until a pressure in the first volume increases to force the fluid through the sponge into the second volume, wherein said method serves for treating incontinence and wherein the first volume is the bladder and the second volume is the urethra, said sponge occluding the fluid from the bladder, until a significant pressure in the bladder forces the fluid into and from the urethra, and wherein said sponge is inserted into a junction between the bladder and the urethra while viewing with a cystoscope.

2. The method according to claim 1, wherein said sponge is made of inert material and has a porosity which regulates the flow of the fluid.

3. The method according to claim 1, comprising indicating conditions of flow of the fluid through the sponge.

4. The method according to claim 1, comprising providing a plurality of sponges having different porosities, and selecting a sponge with a particular porosity for the particular flow regulation desired.

5. A method of treating incontinence comprising the steps of:

preventing leakage and flow of urine from the bladder into the urethra until a pressure increase in the bladder forces the urine into the urethra including inserting a sponge in a flow path between the bladder and the urethra, constructing the sponge with a porosity to occlude urine flow from the bladder into the urethra in the manner of a closed control valve until the increased pressure in the bladder forces the urine through the sponge, into the urethra and wherein said sponge is inserted into a junction between the bladder and the urethra while viewing with a cystoscope.

6. The method according to claim 5, wherein the said porosity of the sponge is selected for occluding flow of urine until bladder pressure forces the urine from the sponge into the urethra.

7. The method according to claim 5, comprising applying a pharmaceutical to the sponge.

8. The method according to claim 5, wherein the sponge is dimensioned and configured to be inserted in the flow path to fill said flow path with said sponge and occlude flow from the bladder to the urethra until bladder pressure increases to force the urine through the sponge.

* * * * *

UNITED STATES PATENT AND TRADEMARK OFFICE
CERTIFICATE OF CORRECTION

PATENT NO. : 7,655,831 B2 Page 1 of 1
APPLICATION NO. : 11/582855
DATED : February 2, 2010
INVENTOR(S) : Arnold S. Prywes It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this

Thirtieth Day of November, 2010

David J. Kappos
*Director of the United States Patent and Trademark Office*